US012749182B2

(12) United States Patent
Reicher

(10) Patent No.: US 12,749,182 B2
(45) Date of Patent: Sep. 29, 2026

(54) DEVELOPMENT OF MEDICAL IMAGING AI ANALYSIS ALGORITHMS LEVERAGING IMAGE SEGMENTATION

(71) Applicant: SYNTHESIS HEALTH INC., Vancouver (CA)

(72) Inventor: Murray Aaron Reicher, Rancho Santa Fe, CA (US)

(73) Assignee: Synthesis Health Inc., Vancouver (CA)

( * ) Notice: Subject to any disclaimer, the term of this patent is extended or adjusted under 35 U.S.C. 154(b) by 383 days.

(21) Appl. No.: 18/302,635

(22) Filed: Apr. 18, 2023

(65) Prior Publication Data

US 2023/0334663 A1 Oct. 19, 2023

Related U.S. Application Data

(60) Provisional application No. 63/332,534, filed on Apr. 19, 2022.

(51) Int. Cl.

| | |
|---|---|
| ***G06T 7/00*** | (2017.01) |
| ***G06T 7/11*** | (2017.01) |
| ***G16H 15/00*** | (2018.01) |
| ***G16H 30/40*** | (2018.01) |
| ***G16H 50/20*** | (2018.01) |

(52) U.S. Cl.

CPC .............. *G06T 7/0012* (2013.01); *G06T 7/11* (2017.01); *G16H 15/00* (2018.01); *G16H 30/40* (2018.01); *G16H 50/20* (2018.01)

(58) Field of Classification Search

None

See application file for complete search history.

(56) References Cited

U.S. PATENT DOCUMENTS

| | | | |
|---|---|---|---|
| 7,646,898 | B1 | 1/2010 | Nowinski et al. |
| 10,210,310 | B2 | 2/2019 | Carolus et al. |
| 10,580,528 | B2 | 3/2020 | Mclaughlin et al. |
| 10,937,164 | B2 | 3/2021 | Steigauf et al. |
| 11,263,749 | B1 | 3/2022 | Purushottam et al. |

(Continued)

FOREIGN PATENT DOCUMENTS

| | | |
|---|---|---|
| CN | 112309528 | 2/2021 |
| CN | 115035089 | 9/2022 |

(Continued)

OTHER PUBLICATIONS

Kim Sung Hyun, KR-20180040287-A (English Translation), System for Interpreting Medical Images Through Machine Learnings (Year: 2018).*

(Continued)

*Primary Examiner* — Miya J Cato

(74) *Attorney, Agent, or Firm* — Knobbe, Martens, Olson & Bear, LLP

(57) ABSTRACT

A medical image may be anatomically segmented, such as by an automated segmentation model, before presentation to a reading physician, who can then step through the anatomical segments which may have already been associated with an initial estimate of whether there is a finding. Based on indications provided by the reading physician, the system may optimize feature detection algorithms of segment-specific diagnostic models that are configured to identify characteristics of medical images of the specific anatomical segments.

16 Claims, 6 Drawing Sheets

*EXAMPLE SEGMENT-SPECIFIC DIAGNOSTICS*

(56) References Cited

U.S. PATENT DOCUMENTS

| | | | |
|---|---|---|---|
| 11,540,794 B2 | 1/2023 | Boddington et al. | |
| 11,574,112 B2 | 2/2023 | Song et al. | |
| 11,664,114 B2 | 5/2023 | Lyman et al. | |
| 12,548,660 B2 | 2/2026 | Reicher et al. | |
| 2007/0282824 A1 | 12/2007 | Ellingsworth | |
| 2008/0146923 A1 | 6/2008 | Mejla et al. | |
| 2008/0205721 A1 | 8/2008 | Udupa et al. | |
| 2009/0092300 A1* | 4/2009 | Jerebko | G06T 7/11 382/128 |
| 2010/0095340 A1 | 4/2010 | Ei et al. | |
| 2013/0251233 A1 | 9/2013 | Yang et al. | |
| 2014/0115020 A1 | 4/2014 | Colaco et al. | |
| 2015/0310358 A1 | 10/2015 | Khabazian | |
| 2016/0121142 A1 | 5/2016 | Zhang et al. | |
| 2016/0154933 A1 | 6/2016 | Ramanathan | |
| 2017/0069084 A1 | 3/2017 | Kubo et al. | |
| 2018/0326149 A1 | 11/2018 | Lipschultz et al. | |
| 2018/0342060 A1* | 11/2018 | Yao | G16H 30/40 |
| 2019/0042703 A1 | 2/2019 | Reicher et al. | |
| 2019/0096060 A1 | 3/2019 | Zhang et al. | |
| 2019/0139218 A1 | 5/2019 | Song et al. | |
| 2019/0139238 A1 | 5/2019 | Wyeth | |
| 2019/0171714 A1 | 6/2019 | Gale et al. | |
| 2019/0188870 A1 | 6/2019 | Park et al. | |
| 2019/0237184 A1 | 8/2019 | Sharma et al. | |
| 2019/0290215 A1 | 9/2019 | Gilbert | |
| 2019/0325249 A1 | 10/2019 | Maraghoosh et al. | |
| 2020/0043600 A1 | 2/2020 | Glottmann et al. | |
| 2020/0178794 A1 | 6/2020 | El-Baz et al. | |
| 2020/0321100 A1 | 10/2020 | Glottmann et al. | |
| 2021/0020303 A1 | 1/2021 | Accomazzi et al. | |
| 2021/0065859 A1 | 3/2021 | McKinney et al. | |
| 2021/0134465 A1 | 5/2021 | Gooßen et al. | |
| 2021/0216822 A1 | 7/2021 | Paik et al. | |
| 2021/0264212 A1 | 8/2021 | Paik et al. | |
| 2021/0282730 A1 | 9/2021 | Singh et al. | |
| 2021/0375435 A1 | 12/2021 | O'Connor et al. | |
| 2022/0037019 A1* | 2/2022 | Covington | G06N 5/04 |
| 2022/0084209 A1* | 3/2022 | Wang | G06T 7/11 |
| 2022/0265233 A1 | 8/2022 | Boddington et al. | |
| 2023/0070444 A1 | 3/2023 | Kartmann et al. | |
| 2023/0108955 A1 | 4/2023 | Weissman et al. | |
| 2023/0334763 A1 | 10/2023 | Reicher | |
| 2023/0335261 A1 | 10/2023 | Reicher et al. | |
| 2023/0343454 A1 | 10/2023 | Chang et al. | |
| 2024/0087724 A1* | 3/2024 | Sawarkar | A61B 5/163 |
| 2024/0153094 A1* | 5/2024 | Liu | G06T 7/0012 |
| 2024/0177836 A1* | 5/2024 | Paik | A61B 5/742 |
| 2024/0312583 A1 | 9/2024 | Amarasingham et al. | |
| 2024/0331354 A1 | 10/2024 | Azad et al. | |
| 2024/0347156 A1 | 10/2024 | Paulett et al. | |
| 2025/0078970 A1 | 3/2025 | Reicher et al. | |
| 2025/0078987 A1 | 3/2025 | Reicher et al. | |

FOREIGN PATENT DOCUMENTS

| | | | |
|---|---|---|---|
| EP | 2561458 | 7/2021 | |
| JP | 2020-523711 | 8/2020 | |
| KR | 10-2018-0040287 | 4/2018 | |
| KR | 20180040287 A * | 4/2018 | G16H 50/50 |
| KR | 10-2019-0102399 | 9/2019 | |
| KR | 10-2374278 | 3/2022 | |
| WO | WO 2014/085918 | 6/2014 | |
| WO | WO 2018/129094 | 7/2018 | |
| WO | WO 2020/8026033 | 2/2020 | |
| WO | WO 2020/056086 | 3/2020 | |
| WO | WO 2022/144360 | 7/2022 | |
| WO | WO 2022/212771 | 10/2022 | |
| WO | WO 2023/205177 | 10/2023 | |
| WO | WO 2023/205179 | 10/2023 | |
| WO | WO 2023/205181 | 10/2023 | |
| WO | WO 2024/102765 | 5/2024 | |
| WO | WO 2024/102832 | 5/2024 | |
| WO | WO 2025/048865 | 3/2025 | |
| WO | WO 2025/155564 | 7/2025 | |

OTHER PUBLICATIONS

International Search Report and Written Opinion for International Application No. PCT/US2023/018991 dated Aug. 8, 2023; 10 pages.

International Search Report and Written Opinion for International Application No. PCT/US2023/018985 dated Aug. 16, 2023; 10 pages.

International Search Report and Written Opinion for International Application No. PCT/US2023/018987 dated Aug. 1, 2023; 11 pages.

International Search Report and Written Opinion for International Application No. PCT/US2023/079001 dated Feb. 29, 2024; 11 pages.

International Search Report and Written Opinion for International Application No. PCT/US2023/079117 dated Mar. 6, 2024; 12 pages.

International Search Report and Written Opinion for International Application No. PCT/US2023/078010 dated May 20, 2024; 8 pages.

International Search Report and Written Opinion for International Application No. PCT/US2025/011591 dated Jul. 2, 2025, 10 pages.

Sugimoto et al., "Extracting clinical terms from radiology reports with deep learning," Journal of Biomedical Informatics 116; In 7 pages (2021).

International Preliminay Report on Patentability for International Application No. PCT/US2023/078010 issued Mar. 4, 2026; 4 pages.

International Search Report and Written Opinion for International Application No. PCT/US2025/046841 mailed Jan. 16, 2026.

Fraunhofer: Analyzing documents faster using artificial intelligence from Fraunhofer. Fraunhofer. (Sep. 1, 2020). Https://www.farunhofer.de/en/press/research-news/2020/september/analyzing-documents-faster-using-artificial-intelligence-from-fraunhofer.html (Year: 2020).

Kalaria et al.: "Comparison-Bot: An Automated Preliminary-Final Report Comparison System," J Digit Imaging (2016) 29:325-330.

* cited by examiner

*EXAMPLE SEGMENT-SPECIFIC DIAGNOSTICS*

DEVELOPMENT OF MEDICAL IMAGING AI ANALYSIS ALGORITHMS LEVERAGING IMAGE SEGMENTATION

BACKGROUND

Development of algorithms for artificial intelligence ("AI") analytics of medical images often requires manual annotation of pathological and normal findings by physician experts or other trained experts. While unsupervised machine learning has been described, this technique has found little use in development of commercial algorithms for medical image analysis. Other methods have been proposed to reduce annotation by experts, but still require at least some human annotation. Manual annotation of medical images is costly, time consuming, and suffers from inter- and intra-observer variations.

There is a need for improved automated medical image segmentation and analysis.

SUMMARY

As discussed herein, a medical image may be anatomically segmented, such as by an automated segmentation model, before presentation to a reading physician, who can then step through the anatomical segments with an indication of normal or abnormal. Based on indications provided by the reading physician (e.g., whether particular segments are normal or abnormal), the system may optimize feature detection algorithms of segment-specific diagnostic models that are configured to identify characteristics of medical images of the specific anatomical segments. Image segmentation and diagnostics may minimize or eliminate the need for manual image annotation and/or manual report generation.

The following description discusses various processes and components that may perform artificial intelligence ("AI") processing or functionality. AI generally refers to the field of creating computer systems that can perform tasks that typically require human intelligence. This includes understanding natural language, recognizing objects in images, making decisions, and solving complex problems. AI systems can be built using various techniques, like neural networks, rule-based systems, or decision trees, for example. Neural networks learn from vast amounts of data and can improve their performance over time. Neural networks may be particularly effective in tasks that involve pattern recognition, such as image recognition, speech recognition, or Natural Language Processing.

Natural Language Processing (NLP) is an area of artificial intelligence (AI) that focuses on teaching computers to understand, interpret, and generate human language. By combining techniques from computer science, machine learning, and/or linguistics, NLP allows for more intuitive and user-friendly communication with computers. NLP may perform a variety of functions, such as sentiment analysis, which determines the emotional tone of text; machine translation, which automatically translates text from one language or format to another; entity recognition, which identifies and categorizes things like people, organizations, or locations within text; text summarization, which creates a summary of a piece of text; speech recognition, which converts spoken language into written text; question-answering, which provides accurate and relevant answers to user queries, and/or other related functions. Natural Language Understanding (NLU), as used herein, is a type of NLP that focuses on the comprehension aspect of human language. NLU may attempt to better understand the meaning and context of the text, including idioms, metaphors, and other linguistic nuances. As used herein, references to specific implementations of AI, NLP, or NLU should be interpreted to include any other implementations, including any of those discussed above. For example, references to NLP herein should be interpreted to include NLU also.

A system of one or more computers can be configured to perform the below example operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Example 1. A computerized method, performed by a computing system having one or more hardware computer processors and one or more non-transitory computer readable storage device storing software instructions executable by the computing system to perform the computerized method comprising: for each of a plurality of medical images: accessing the medical image; applying a segmentation algorithm to the medical image to determine a plurality of segments indicated in the medical image, displaying the medical image on a display device of a user; receiving input from the user indicating whether each of the plurality of segments show a finding or no finding; and storing the indications of segments with findings vs no findings and the segment boundaries in association with the image in a training data set; for each of the plurality of segments: training a segment-specific diagnostic model to detect findings in the segment of medical images not included in the plurality of medical images, wherein the segment analysis model accesses the training data set to identify a first set of medical images with the segment identified as no finding and a second set of medical images with the segment identified as finding detected, and trains the segment-specific diagnostic model based on differences between the first and second sets of medical images.

Example 2. The method of Example 1, further comprising: accessing a medical image not included in the plurality of medical images; applying the segmentation algorithm to the medical image to determine the plurality of segments of patient anatomy indicated in the medical image; for each of the segments identified in the medical image: selecting a segment-specific diagnostic model associated with the segment; applying the segment-specific diagnostic model to at least portions of the medical image associated with the segment, wherein the segment-specific diagnostic model provides an indication of whether the segment is more likely normal or abnormal.

Example 3. The method of Example 1, wherein the plurality of segments of patient anatomy include one or more of: lungs, vasculature, cardiac, mediastinum, pleura, or bone.

Example 4. The method of Example 1, wherein the plurality of segments of patient anatomy include one or more of: digestive system, musculoskeletal system, nervous system, endocrine system, reproductive system, urinary system, or immune system.

Example 5. The method of Example 1, wherein the segments are associated with corresponding sections of a medical report.

Example 6. A computerized method, performed by a computing system having one or more hardware computer processors and one or more non-transitory computer readable storage device storing software instructions executable by the computing system to perform the computerized method comprising: accessing a medical image; applying a segmentation algorithm to the medical image to determine a plurality of segments of patient anatomy indicated in the medical image; for each of the segments identified in the medical image: selecting a segment-specific diagnostic model associated with the segment; applying the segment-specific diagnostic model to at least portions of the medical image associated with the segment, wherein the segment-specific diagnostic model provides an indication of whether the segment include has a finding or has no finding.

Example 7. The method of Example 6, wherein the plurality of segments are stored in data structure in association with a type of the medical image.

Example 8. The method of Example 6, further comprising: wherein the segmentation algorithm accesses a medical report associated with the medical image to determine whether there is a finding or no finding for each of the segments indicating in the medical report.

Example 9. The method of Example 8, wherein said determining whether there is a finding or no finding for each of the segments indicating in the medical report is based at least partly on natural language processing of textual descriptions associated with respective segments.

Example 10. The method of Example 6, wherein the segment-specific diagnostic models are trained using manual annotation of the segments.

Example 11. The method of Example 6, wherein the segment-specific diagnostic models are trained using itemized reports wherein at least one report item corresponds to a segment defined in an image.

Example 12. The method of Example 6, wherein the segment-specific diagnostic models are trained using one or more artificial intelligence algorithms to classify items in a medical report as finding or no finding.

Example 13. The method of Example 6, further comprising: displaying, in a user interface, an indication of any segments with findings.

Example 14. The method of Example 6, further comprising: prepopulating an itemized report with the indications of findings and associated segments.

Example 15. The method of Example 14, wherein the segments associated with findings are indicated in the report. The method of claim 14, wherein the segments associated with findings include a link or reference to a medical image associated with the finding.

Example 16. The method of Example 6, wherein the segment-specific diagnostic model determining indications of finding vs no finding based on one or more of an indication or a clinical question.

Example 17. The method of Example 6, wherein at least one of the segments is defined by human anatomy or any other imaging finding, such as a tube.

DETAILED DESCRIPTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with certain specific embodiments. Furthermore, embodiments of the invention may include several novel features, no single one of which is solely responsible for its desirable attributes or which is essential to practicing the inventions herein described.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
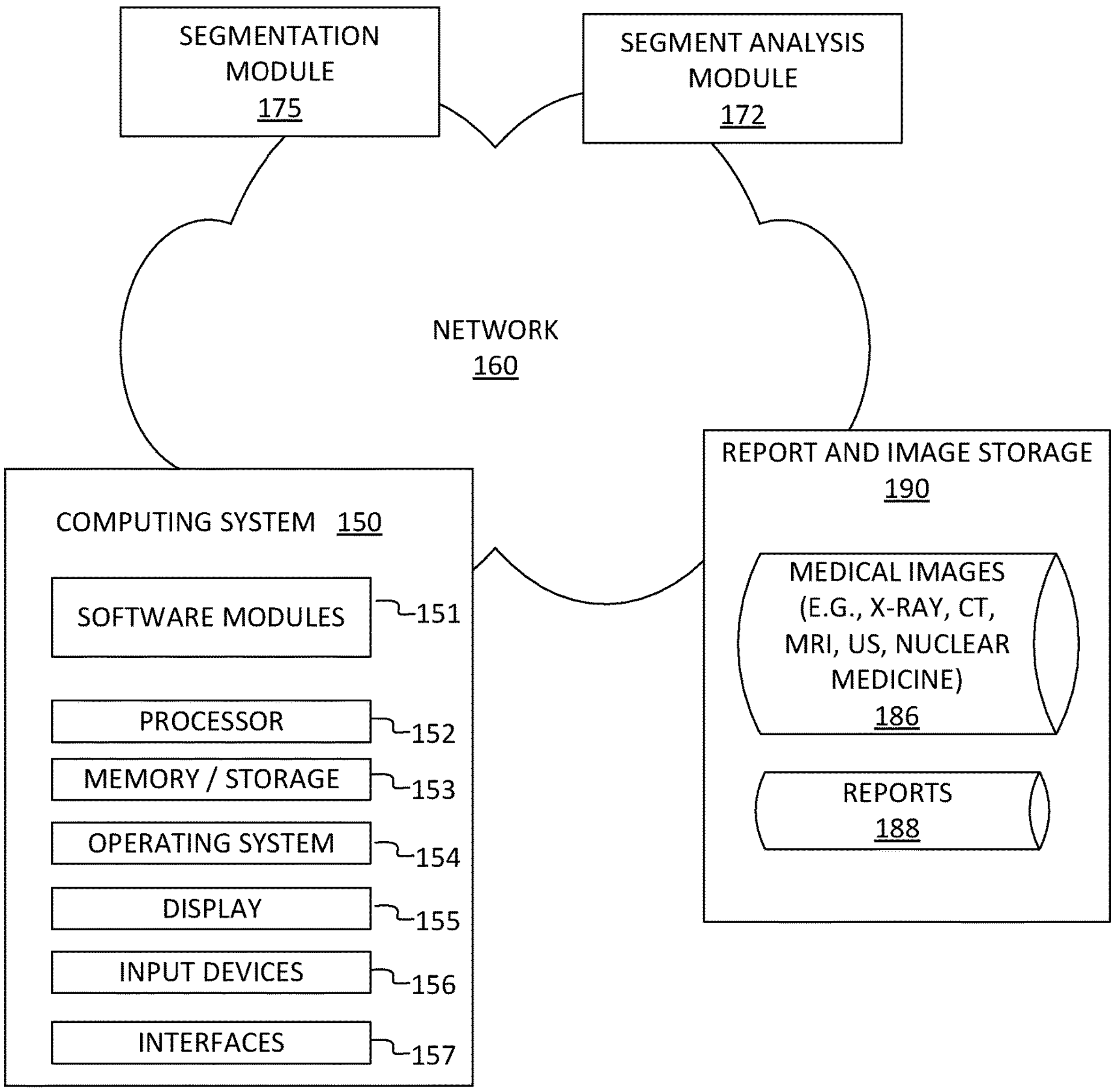
FIG. 1 illustrates an example computing system (also referred to herein as a "computing device" or "system").

The systems and methods discussed herein may be performed by various computing systems, which are referred to herein generally as a viewing device or computing system (such as computing system 150 of FIG. 1). A computing system may include, for example, a picture archiving and communication system ("PACs") or other computing system configured to display images, such as computed tomography ("CT"), magnetic resonance imaging ("MRI"), ultrasound ("US"), radiography ("XR"), positron emission tomography ("PET"), nuclear medicine ("NM"), fluoroscopy ("FL"), photographs, and/or any other type of image. Any of the computer processing discussed herein, such as application of artificial intelligence (AI")" and/or development or updating of AI algorithms, may be performed at the computing system and/or at one or more backend or cloud devices, such as one or more servers. Thus, even if a particular computerized processes is described herein as being performed by a particular computing system (e.g., a PACS or sever), the processes may be performed partially or fully by other devices.

Example System

FIG. 1 illustrates an example computing system 150 (also referred to herein as a "computing device 150" or "system 150"). The computing system 150 may take various forms. In one embodiment, the computing system 150 may be a computer workstation having modules 151, such as software, firmware, and/or hardware modules. In other embodiments, modules 151 may reside on another computing device, such as a web server, and the user directly interacts with a second computing device that is connected to the web server via a computer network.

In various embodiments, the computing system 150 comprises one or more of a server, a desktop computer, a workstation, a laptop computer, a mobile computer, a Smartphone, a tablet computer, a cell phone, a personal digital assistant, a gaming system, a kiosk, any other device that utilizes a graphical user interface, including office equipment, automobiles, industrial equipment, and/or a television, for example. In one embodiment, for example, the computing system 150 comprises a tablet computer that provides a user interface responsive to contact with a human hand/finger or stylus.

The computing system 150 may run an off-the-shelf operating system 154 such as a Windows, Linux, MacOS, Android, iOS, or other. The computing system 150 may also run a more specialized operating system which may be designed for the specific tasks performed by the computing system 150.

The computing system 150 may include one or more hardware computing processors 152. The computer processors 152 may include central processing units (CPUs) and may further include dedicated processors such as graphics processor chips, or other specialized processors. The processors generally are used to execute computer instructions based on the software modules 151 to cause the computing device to perform operations as specified by the modules 151.

The various software modules 151 (or simply "modules 151") may be provided on a computer readable medium, such as a compact disc, digital video disc, flash drive, or any other tangible medium. Such software code may be stored, partially or fully, on a memory device of the executing computing device for execution by the computing device. The application modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Visual Basic, HTML, C, C++, or C #. While "modules" are generally discussed herein with reference to software, any modules may alternatively be represented in hardware or firmware. Generally, the modules described herein refer to logical modules that may be combined with other modules or divided into sub-modules despite their physical organization or storage.

The computing system 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The computing system 150 may also include or be interfaced to one or more display devices 155 that provide information to the users. A display device 155 may provide for the presentation of GUIs, application software data, and multimedia presentations, for example. Display devices 155 may include a video display, such as one or more high-resolution computer monitors, or a display device integrated into or attached to a laptop computer, handheld computer, Smartphone, computer tablet device, or medical scanner. In other embodiments, the display device 155 may include an LCD, OLED, or other thin screen display surface, a monitor, television, projector, a display integrated into wearable glasses, such as a virtual reality or augmented reality headset, or any other device that visually depicts user interfaces and data to viewers.

The computing system 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The computing system 150 may also include one or more interfaces 157 which allow information exchange between computing system 150 and other computers and input/output devices using systems such as Ethernet, Wi-Fi, Bluetooth, as well as other wired and wireless data communications techniques.

The modules of the computing system 150 may be connected using a standard based bus system. The functionality provided for in the components and modules of computing system 150 may be combined into fewer components and modules or further separated into additional components and modules.

In the example of FIG. 1, the computing system 150 is connected to a computer network 160, which allows communications with various other devices, both local and remote. The computer network 160 may take various forms. It may be a wired network or a wireless network, or it may be some combination of both. The computer network 160 may be a single computer network, or it may be a combination or collection of different networks and network protocols. For example, the computer network 160 may include one or more local area networks (LAN), wide area networks (WAN), personal area networks (PAN), cellular or data networks, and/or the Internet.

Various devices and subsystems may be connected to the network 160. For example, one or more medical imaging device that generate images associated with a patient in various formats, such as Computed Tomography ("CT"), magnetic resonance imaging ("MRI"), Ultrasound ("US"), (X-Ray) ("XR"), Positron emission tomography ("PET"), Nuclear Medicine ("NM"), Fluoroscopy ("FL"), photographs, illustrations and/or any other type of image. These devices may be used to acquire images from patients, and may share the acquired images with other devices on the network 160. Medical images may be stored in any format, such as an open source format or a proprietary format. A common format for image storage in the PACS system is the Digital Imaging and Communications in Medicine (DICOM) format.

Example AI Segmentation and Analysis

In the example of FIG. 1, the computing system 150 is configured to execute one or more of a segmentation module 175 and/or segment analysis module 172. In some embodiments, the modules 172, 175 are stored partially or fully in the software modules 151 of the system 150. In some implementations, one or more of the modules 172, 175 may be stored remote from the computing system 150, such as on another device that is accessible via a local or wide area network (e.g., via network 160). In an example implementation, the segmentation module 175 analyzes medical images and outputs information identifying segments within the medical images. As discussed further below, the segmentation process performed by the segmentation module 175 may include one or more preprocessing operations, in addition to various segmentation operations. The segment module 175 may output segment information associated with a medical image (or medical images) that may be stored with and/or provided to various other systems for various purposes. As discussed herein, the segment information, which generally indicates a segment identifier and location of the segment in the medical image, may be stored in DICOM header information of the image or stored separately with a correlation to the medical image. In general, the segment analysis module 172 executes segment-specific artificial intelligence algorithms that are trained or tuned with reference to the specific segment. For example, a first anatomical segment may be associated with a first segment analysis model (e.g., an artificial intelligence algorithm) that may be executed by the segment analysis module 172 when an image including the first anatomical segment is being processed. The first segment analysis model may not be used for any other anatomical segments, though, as it is trained to identify characteristics specifically of the first anatomical segment. Similarly, a second segment analysis model may be executed by the segment analysis module 172 when an image including a second anatomical segment is being processed, and the second segment analysis model may not be used for any other anatomical segments. In some embodiments, segment-specific analysis models may be associated with any other characteristics of a medical image, such as imaging modality, image dimensions, patient characteristics, etc. Thus, segment-specific analysis models may be finely tuned to identify abnormalities in particular image segments.

In the example of FIG. 1, a report and image storage 190 stores various modalities of medical images 186 and medical reports 188. In an example implementation, when a new medical image acquired via medical imaging equipment, is stored in the medical images 186 an image segmentation and analysis process is initiated. In some embodiments, the computing system 150 may be notified of the available image and initiate automatic segmentation and analysis of the medical image. The segmentation module 175 and segment analysis module 172 may then access the image at the image storage 190 and provide segmentation and segment analysis results to the computing system 150 and/or other systems.

As discussed further below, in some embodiments a medical imaging report may generated and at least partially pre-populated with results of the segment analysis, such as to indicate whether each of the identified segments is abnormal or normal (based on execution of the segment-specific analysis models on the corresponding image segments). Such pre-populated reports may be stored with the reports 188 and made accessible to other devices, such as the computing system 150. In some embodiments, the segmentation and analysis performed by modules 175, 172 may be initiated automatically, without user intervention, upon receipt of a new medical image at the storage 190 and/or by other processes.

The modules 172, 175 may each include one or more machine learning models that are generally usable to evaluate input data to provide some output data. As noted above with reference to software modules 151, the modules may comprise various formats and types of code or other computer instructions. In some implementations, the modules are accessed via the network 160 and applied to various formats of data at the computing system 150. In some embodiments, the various modules 172, 175 may be executed remote from the computing system 150, such as at a cloud device (e.g., one or more servers that is accessible view the Internet) dedicated for evaluation of the particular module (e.g., including the machine learning model(s) in the particular module). Thus, even if a particular computerized processes is described herein as being performed by a particular computing device (e.g., the computing system 150), the processes may be performed partially or fully by other devices.

Example Image Segmentation

The segmentation module 175 may include one or more medical image segmentation algorithms configured to access particular input and provide a particular output. For example, a segmentation algorithm may utilize machine learning, convolutional neural networks (CNNs), and/or other artificial intelligence configured to associate the areas of patient anatomy (e.g., 2D or 3D) in one or more medical images with anatomical segments. The anatomical segments may be predefined (e.g., by the software provider or user) or may be identified by the user. In one example, the segmentation module 175 may initially preprocess a medical image to remove, artifacts, normalize the image (e.g., color, contrast, etc.), register the image (e.g., rotate, resize, and/or shift the image), and/or other processes. The image may then be processed by a feature selection algorithm that detects features such as shapes, textures, gradients, etc. that may be useful in identifying features of the medical image, such as by defining edges of anatomical segments.

In some implementations, an initial segment is identified, such as by selecting a predefined or dynamically determined point of the medical image and growing the region to identify borders. Boundaries of the initial segment may then be identified via techniques such as thresholding, region growing, graph-based methods, edge-based methods, active contours or snakes, watershed algorithms, and the like.

Next, additional segments may be identified around the initial segment in a similar manner, until no further segments have been identified in the image. In some implementations, one or more postprocessing algorithms may be used to improve accuracy of segmentation and/or to smooth boundaries between segments, such as by using morphological operations or smoothing filters.

The segment information (or "segment metadata") for the image may then be stored in association with the image (or as part of the same image file). Segment information may indicate a boundary and a segment identifier for each identified segment. Some embodiments, segment metadata may include additional information, such as particular features identified in the segment. As an example, the segment metadata for a chest x-ray may include a set of two-dimensional coordinates defining a boundary for a lungs segment associated with a lungs identifier (e.g., segment type: Lungs), and similar sets of two-dimensional coordinates and identifiers for other segments. In some embodiments, the boundary of a segment includes a set of three-dimensional coordinates, such as to identify a 3D area of an MRI or other volumetric image. In some embodiments, boundaries for two or more identified segments may overlap within a single image and/or across multiple images (e.g., three-dimensional segments that overlap across multiple slices of a multislice imaging volume).

The above-described image segmentation is provided as an example of segmentation processes. In other embodiments, other segmentation algorithms and outcomes may be used to segment images in conjunction with the systems and methods discussed herein.

Example Technical Improvements

Certain example implementations discussed herein are provided with reference to specific types of images. However, the systems and methods are not limited to those example implementations and are usable with any type of medical image. In addition, while many examples are discussed with reference to a medical image, this term is not limited to a single image file. For example, a medical image could be a single image file or could be a series of image files, such as slices of a CT volume, or a set of pixel or voxel values that may be reconstructed to generate various 2D or 3D images or representations. Some examples discussed herein are with reference to a chest radiograph. However, these example systems and methods can be applied to any type of medical image or even to non-medical images. In one example described below, a user wishes to develop an algorithm that determines whether specific regions on a chest radiograph are normal or abnormal so that a clinical report can be automatically generated listing the regions and whether they are normal or abnormal. This may benefit human report generator or editors, such as reading physicians, in multiple ways including, for example:

- they could focus attention on the areas found to be abnormal,
- they would not need to describe areas found to be normal because the report could be pre-populated with appropriate negative results for those areas,
- they could track abnormalities by specific region for teaching and public health purposes, and/or
- when they disagree with the algorithm's findings, they could provide region-specific feedback so that the algorithm could more efficiently improve.

Example Systems and Methods

In one example implementation, a computing system is configured to develop and implement an AI algorithm for assisting in reading and reporting of chest radiographs. The system may employ a cloud-based medical image reading and reporting system designed to display chest radiographs and associated report templates, then receive input from a reading physician, e.g., via speech recognition, dictation, typing, or other methods of text input.

Figure 2:
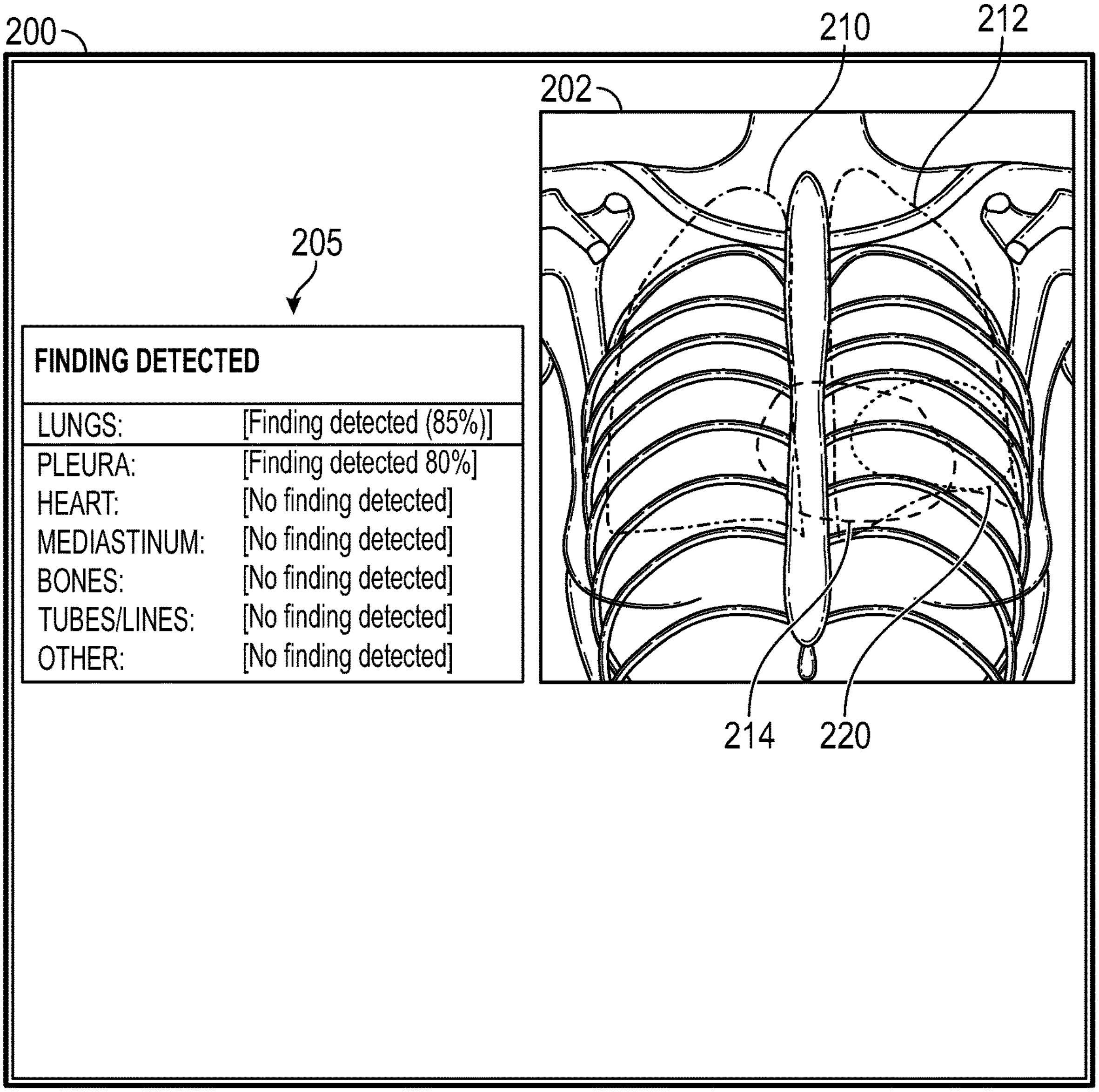
FIG. 2 illustrates an example segmentation results user interface indicating segments that were automatically identified and those including a finding or no finding.

FIG. 2 illustrates an example segmentation results user interface 200 indicating segments that were automatically identified, such as by the segmentation module 175. For the sake of simplicity, the chest image in FIG. 2 shows the boundaries of only the left lung 212, right lung 210, and cardiac segments 214, along with a region 220 of detected abnormality. In the example of FIG. 2, the segmentation results 205 lists each of multiple segments identified in the medical image 202 (e.g., a chest radiograph in this example), along with a corresponding confidence level for each of the identified findings. In some embodiments, each segment may be listed in the segmentation results, which may be stored in a database and/or output as a document or electronic message. For example, the results 205 may be output as a DICOM Structured Report, electronic message (proprietary format, HL-7, or FHIR), PDF or MSWord document, image, or other similar output. In some embodiments that results from one or more segments may be combined. In the example of FIG. 2, the left lung and right lung results are combined in results 205. In some results, the report of finding vs. no finding may pertain to the entire exam as well as or instead of individual segments. In some instances, the finding vs no finding report may be configured to relate to a specific diagnosis or spectrum of diagnoses (no finding suspicious for cancer, or for infectious disease, or for tuberculosis). In some embodiments, the finding vs no finding report may be responsive to the clinical indication (reason for the examination). For example, no finding suspicious for a fracture in a patient with a history of trauma. In some embodiments, a confidence level may be reported, and in some cases, the only report may be whether a finding is detected or not. In some instances, the finding vs no finding may pertain not to human anatomy but to other structures in the image such as no tubes/lines vs tubes/lines detected or no laterality markers vs laterality markers detected.

The results 205 indicate the confidence level that an abnormality was detected in the corresponding segment (for example, the confidence level that a finding was detected in at least one lung is 85%). In addition, or alternatively, a report may indicate the confidence level of a finding detected within a specified boundary or other marker that shows where the system detected a finding.

In some implementations, a confidence level associated with the identified segment boundaries may be provided. For example, a 60% confidence level associated with a segment may indicate that the segmentation of that segment is not entirely accurate or inclusive. In some embodiments, the user may scroll through the segments (or select the segments in other manners) in the listing of the segments in the segmentation results 205 to update the segment boundaries in the image 202 and/or initiate re-segmentation. In response to user selection of another segment, the segment boundaries and/or other visualizations associated with that segment may be automatically updated in the medical image 202.

In some embodiments, the segments included in the segmentation results may correspond to headings (or "regions") of a medical imaging report for the particular image type. For example, the segmentation module may determine that a medical image is a chest radiograph, such as based on metadata associated with the image (e.g., in the DICOM information associated with the image) and, based on the determined image type, determine segments that are expected to be included in the image. The segmentation module may then attempt to identify each of the expected segments in the medical image and provide segmentation results including headings for each of the segments in a user interface similar to user interface 200. In some embodiments, the system may work in concert with a reporting system, so that when results are provided, the results for each segment may be mapped into specific regions of a report template linked to the particular exam type. In some cases, when such a mapping occurs, the line items in the report where no finding is detected may be prepopulated with predefined text and the line items describing segments where an abnormality is detected may be replaced or partially replaced with the output from the algorithm. For example, a report for a Chest Radiograph may begin with the following template:

FINDINGS:
LUNGS: [No significant pulmonary parenchymal abnormalities.]
HEART: [No cardiac contour abnormality or cardiomegaly.]
MEDIASTINUM: [No visible mass or adenopathy.]
PLEURA: [No effusion or pleural thickening.]
BONES: [No fracture or significant osseous lesion.]
TUBES/LINES: [None.]
OTHER: [Negative.]

Subsequent to mapping of the results into the report template, the report may appear as follows:

FINDINGS:
LUNGS: [Finding detected]
HEART: [No cardiac contour abnormality or cardiomegaly.]
MEDIASTINUM: [No visible mass or adenopathy.]
PLEURA: [Finding detected].
BONES: [No fracture or significant osseous lesion.]
TUBES/LINES: [None.]
OTHER: [Negative.]

The reporting system may be designed to highlight (in some fashion) the line items where a finding is detected, to otherwise bring the finding to the reader's attention (such as an audio message), to automatically bring the computer cursor to the field where a finding is detected, or to automatically skip forward or backward between on the fields where a finding is detected, thus expediting reporting in conjunction with the segment detection algorithm.

Figure 3:
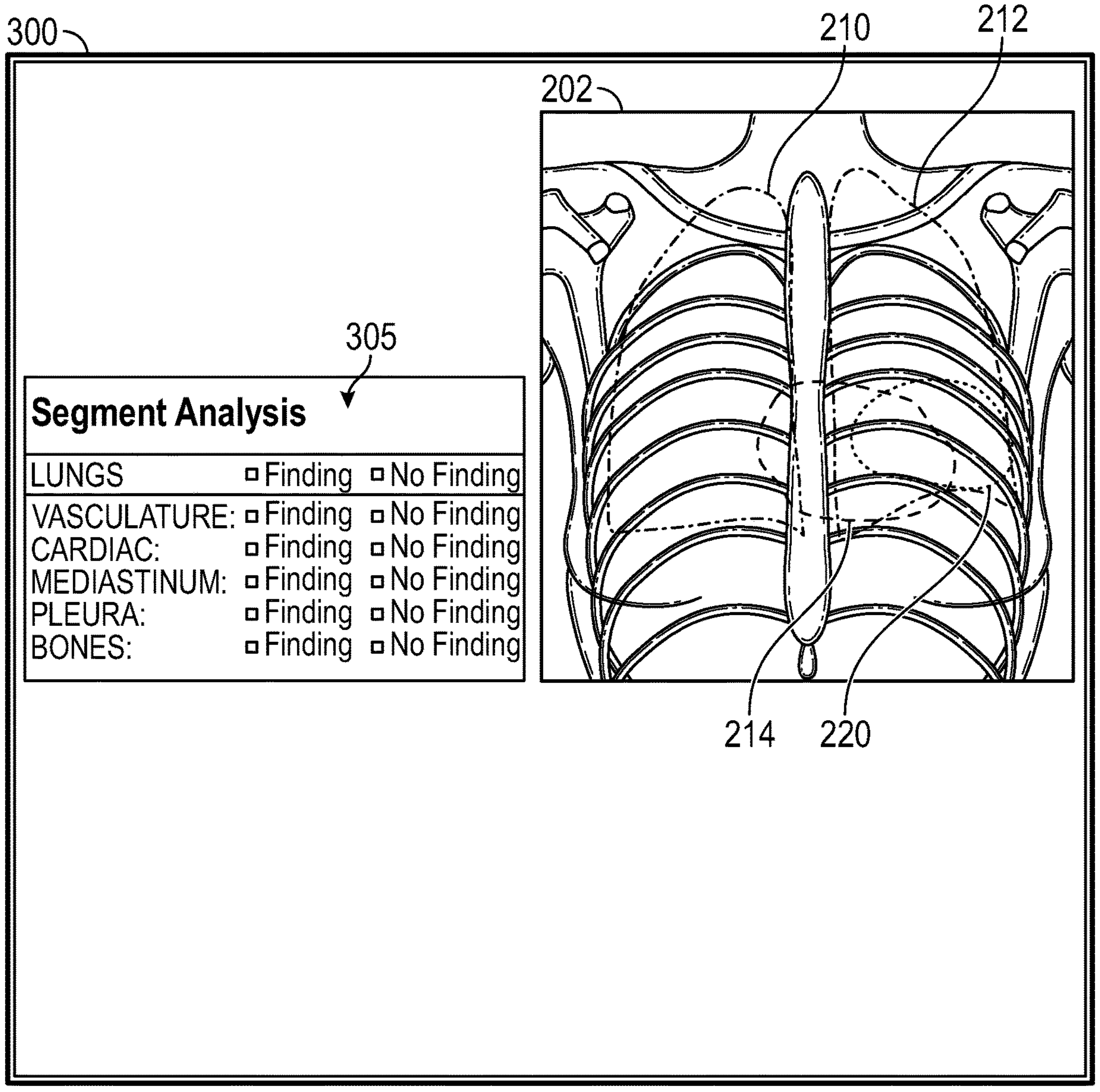
FIG. 3 is an example training user interface.

FIG. 3 is an example training user interface 300. In this example, the medical image 202 is illustrated, along with indications of segment outlines 210, 212 and 214 associated with a currently selected segment (lungs in this example). This user interface is configured to receive input from the user (e.g., a reading physician) indicating a state of each of the segments, where the state in this example indicates either finding or no finding. In this example, the state of each of the segments may be selected by checking the boxes next to the finding or no finding indicators, or other user inputs may be used to identify state or other characteristics of the current image segment. In some embodiments, the finding vs no finding state may be selected as a default. The state information gathered from this user interface may then be made accessible to the segment analysis module 172, such as by adding to a training data set, for generating and/or tuning segment-specific analysis models.

In some embodiments an input to the system may not be via manual selection of finding vs. no finding, but instead in using report analytics such as but not limited to natural language processing to identified reported findings for each line item. For example, if a reading physician changes the text associated with pleura the system may learn that the pleura was specified as having a finding. Alternatively, the content of the text or audio input may be interpreted to understand the finding vs. no finding state of each line item, even if the report itself does not organized with specific line items. For example, a reading physician may state, "The cardiac silhouette, pulmonary structures, pleura and bones are normal, from which the system determine:

LUNGS: No finding
PLEURA: [No finding
HEART: [No finding detected]
MEDIASTINUM: [Indeterminant]
BONES: [No finding detected]
TUBES/LINES: [Indeterminant]
OTHER: [Indeterminant]

The segment analysis module 172 may periodically regenerate and/or retrain segment-specific models for diagnosing segments of medical images. For example, the segment analysis module 172 may access medical images and/or receive other anatomically specific information, without the need for user annotation, and learn to distinguish normal from abnormal in the anatomically segmented regions. Thus, when deployed to clinical use, the segment analysis module 172 may detect an abnormality in one or more anatomically segmented regions using segment-specific models that are trained based on expert analysis of other medical images.

In one example implementation, training data associated with the segments illustrated in FIG. 3 may be received from multiple expert readers. The segment analysis module 172 may train a segment analysis model for each of the segments based on the findings (e.g., finding or no finding) associated with the particular segment from each of the multiple expert readers. In this way, the segment-specific models are optimized to more accurately identify abnormalities in other medical images (e.g., that are not part of the training data) that have similar features to the abnormal segments of the training data.

Figure 4:
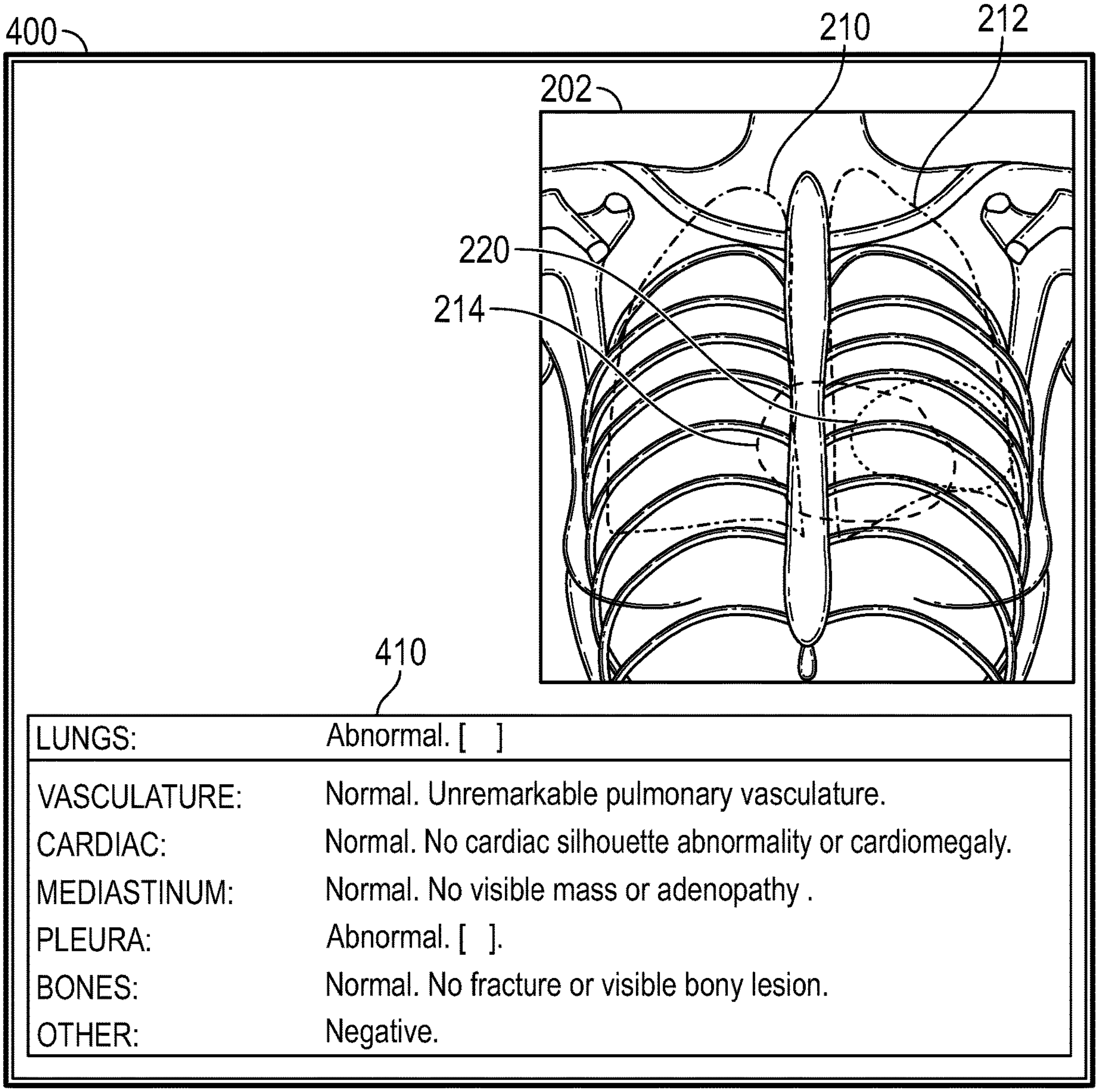
FIG. 4 is a report generation user interface that includes an example portion of a pre-populated report.

FIG. 4 is a report generation user interface 400 that includes an example portion of a pre-populated report 410. The pre-populated report includes results of artificial intelligence processing applied to the medical image(s), such as segmentation (e.g., by the segmentation module 175) and segment state (e.g., by the segment analysis module 172). As a result, the reading physician may see at a glance which segments of the chest were found to be abnormal. In one embodiment, instead of, or in addition to, displaying the report, the system may provide an audio output indicating a particular segment is abnormal, so that the reading physician may be responsive using speech recognition without needing to first look at the report, thus avoiding diverting focus from the image.

The example report generation user interface 400 includes report headings that correspond directly to segments identified in the medical image (e.g., a chest radiograph in this particular example), along with the automatically generated diagnostic state (or findings), such as may be generated by the segment analysis module 172. In this example, the lungs and pleura segments are indicated as having abnormal features, while the other segments are indicated as normal. In some embodiments, the user may select one or more of the headings to cause updates to the corresponding segment boundaries on the medical image 202. In the example of FIG. 4, the lungs heading is selected and so the segment outlines 210, 212 associated with the lungs segment identified in the medical image 202 are displayed. With this automatically generated segment-specific diagnostic information, a user may choose to focus their review on only those segments with abnormal findings, such as by selecting one of the abnormal segments to initiate display of markers outlining that segment in a corresponding medical image. In the example of FIG. 4, the user may provide additional description of a selected image segment (e.g., the lungs section is selected in user interface 400) via any input means, such as voice description.

In some embodiments, the report headings included in the report 410 are selected based on the type of medical image. For example, for a medical image identified as a chest radiograph, a predefined set of segments may be identified by the segmentation module and included as corresponding headings in the findings section of the medical report. In some embodiments, the headings included in the medical report are only those corresponding to segments that were identified by the segmentation module, which may include additional or fewer segments than are typically associated with the image type. In some embodiments, the segments identified by the segmentation module may not have a 1:1 correspondence with the report headings, but may be mapped in another manner, such as 2:1 (e.g., two segments are mapped to a single report heading), 1:2 (e.g., one segment is mapped to each of two report headings), or other mappings.

In some embodiments, the system may present a medical image with any abnormal segment(s) highlighted or outlined. For example, a reading physician (or other user) may use a mouse or touchscreen to point at a highlighted abnormal segment, then use speech recognition to describe an abnormality, in which case the description might not include a description of the anatomical location, which the system already knows. As a result, the description may be briefer and may automatically be placed in the appropriate section of the report. In some embodiments, when there are multiple segments found to be abnormal by the AI processing (e.g., by the segment analysis module 172), the abnormal segments may be sequentially highlighted in the order in which they appear in the report, so that after the physician provides a description of the first abnormal segment, the highlight of the second abnormal segment automatically appears. For example, a physician reading preference might determine of normal segments are outlined in sequence as well.

In some embodiments, information provided by the user completing a report, such as via a user interface 400, may be included in training data that is used to improve segment analysis models. For example, if the user determines that the lungs segment is actually normal in the example of FIG. 4, the report may be changed to indicate the lungs show no finding and the change from finding to no finding may be provided as feedback to the segment analysis model, which may improve future false detections. In some embodiments, a minimum experience level of a user is required for the updates or feedback to be provided to the segment analysis module 172 and used in updating the segment analysis module.

In some embodiments, when a physician describes an abnormality that involves a segment, such as when adding further description of segments in the pre-populated report in FIG. 4, even if a selected segment overlaps in the image with another segment, the system can automatically classify the segment location of the abnormality because it knows which highlighted segment the physician is describing. For example, if the physician points or cursor or otherwise uses a graphic user interface to indicate a portion of the image that corresponds to overlapping segments (such as the left lung, heart, and a rib), the system would narrow the potential segments to these three choices, then use other factors (such as in which segment the system believes the finding to be or interpretation of the text the physician provides) to make the proper segment selection. Thus, input from the user may associated with the appropriate segment for purposes of updating a segment-specific diagnostic model that improves diagnostic capabilities and/or accuracy of the model over time and may also be used for the purpose of report generation.

In addition to use by a reading physician, the various systems and methods discussed herein may benefit technologists and other user roles, such as emergency physicians and others that may view and interpret medical images without the benefit of a radiologist expert. For example, by pointing out to a technologist that an abnormality exists in a particular area of segmented anatomy, the system may contribute to the expertise of the technologist and may stimulate modifications in additional medical imaging and/or procedures that are performed. For example, a technologist that receives information that there is a pleural abnormality may, based on a protocol, then obtain a lateral decubitus view of the chest.

In an example use in an emergency room, the physician may view a chest radiograph that was urgently obtained and receive information that there is no detected abnormality, allowing the patient to be appropriately triaged. In addition, the system may provide information that one or more segments are abnormal, causing the patient to be triaged differently, or causing the need for an expert consultation. In regions of the world where radiologists are in short supply, the system could be used to triage which images are sent for expert review.

Figure 5:
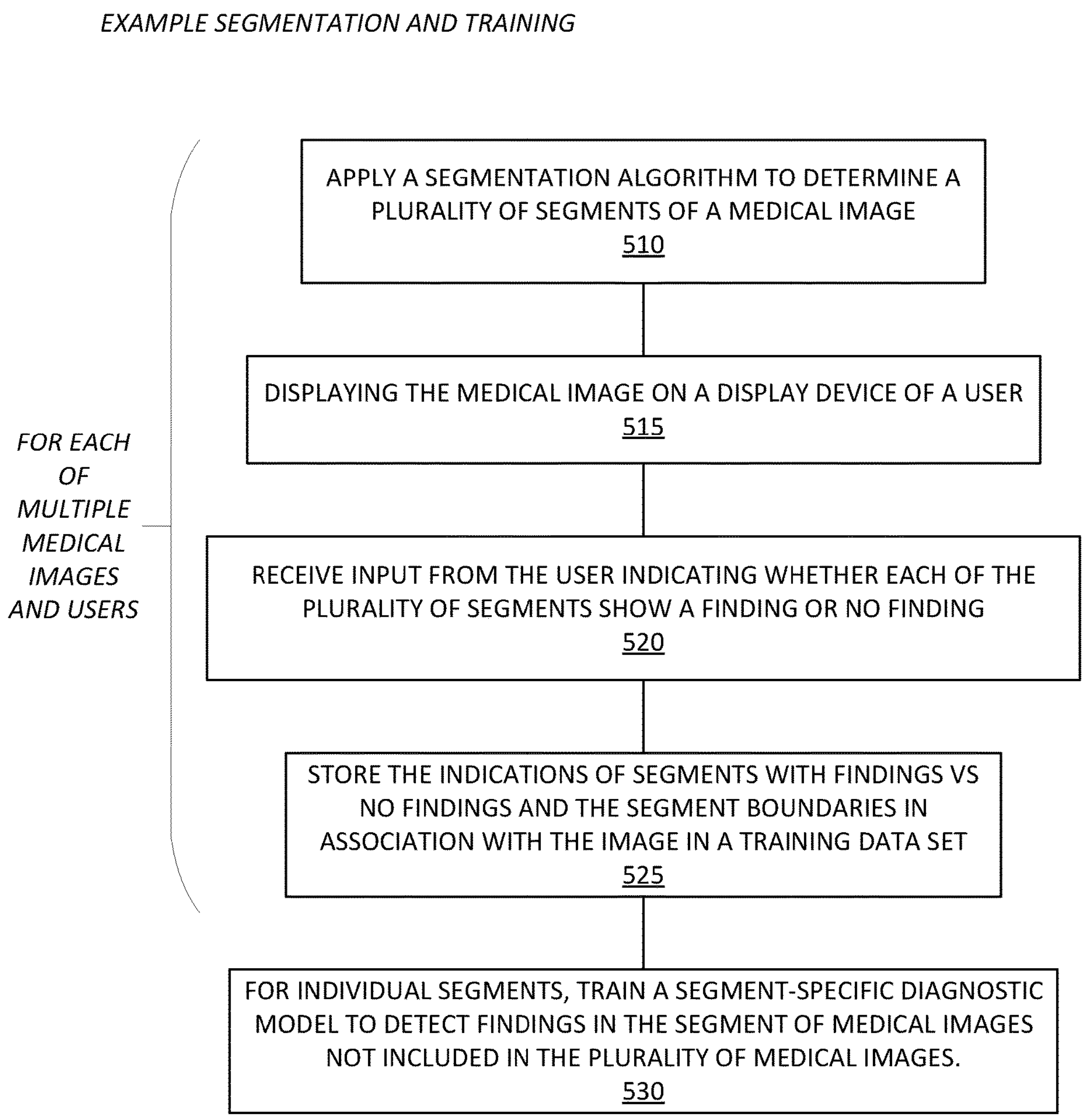
FIG. 5 is a flowchart illustrating one embodiment of an example method of training segment-specific diagnostic models.

FIG. 5 is a flowchart illustrating one embodiment of an example method of training segment-specific diagnostic models. The process discussed with reference to FIG. 5 may be performed, for example, by the system 150, the segmentation module 175, the segment diagnostic module 172, and/or other computing devices or configurations thereof. Depending on the embodiment, the processes discussed with reference to FIG. 5 may include fewer or additional blocks and/or the blocks may be performed in order different than is illustrated.

Blocks 510-525 may be performed for each of a plurality of medical images that are reviewed by multiple users, such as expert readers at various locations and at different times. For example, blocks 510-525 may be performed in response to a user (e.g., a radiologist using the computing system 150 or similar device) requesting display of a medical image. Beginning at block 510, the system applies a segmentation algorithm to the medical image to determine a plurality of segments. At block 515, the medical image is displayed on a display device, in some implementations with indications of segments (e.g., visual indications overlaid on the medical image) that have been identified by the segmentation algorithm. At block 520, the system receives input from the user indicating which of the plurality of segments include a finding. For example, the user may indicate for a first segment that there is no finding (e.g., no abnormality in the segment) and for second segment may indicate that there is a finding (e.g., some abnormality in the segment). In some implementations, all segments default to "no finding," so if the user doesn't provide separate input regarding a finding for a particular segment the segment will be associated with an indication of "no finding" from the user. Further information regarding segments with a finding may also be provided by the user and associated with the segment, and/or used in training segment-specific diagnostic models. At block 525, the system stores the provided indications of findings vs no findings provided by the user, along with the segment boundaries and/or other segment information, in association with the image in a training data set. Thus, the training data set may include hundreds, thousands, hundreds of thousands, etc. of images that have associated segments and the indications of findings within the segments provided by a plurality of different users. In some embodiments, the same medical image may be analyzed by multiple users and the separate indications of findings by the multiple users are stored in the training data set. Based on the training data set, the system may generate, update, and/or refine segment-specific diagnostic models for each segment. As discussed elsewhere herein, these segment-specific diagnostic models may more accurately identify abnormalities in the associated segment when applied to that same image segment in later acquired medical images.

Figure 6:
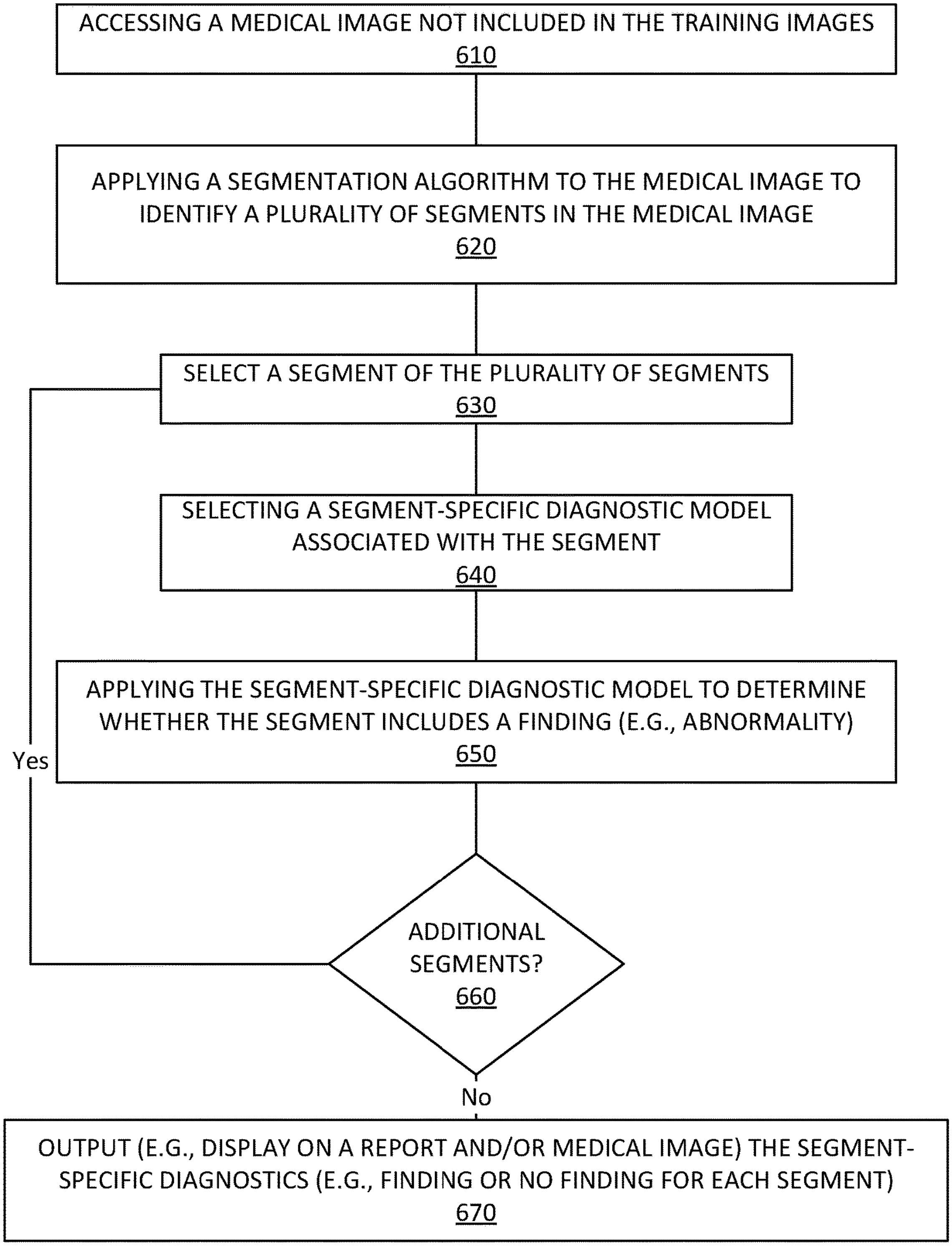
FIG. 6 is a flowchart illustrating one embodiment of an example method of generating automated diagnostic information associated with a medical image, such as based on segment-specific diagnostic models that are developed as discussed above.

FIG. 6 is a flowchart illustrating one embodiment of an example method of generating automated diagnostic information associated with a medical image, such as based on segment-specific diagnostic models that are developed as discussed above. The process discussed with reference to FIG. 6 may be performed, for example, by the system 150, the segmentation module 175, the segment diagnostic module 172, and/or other computing devices or configurations thereof. Depending on the embodiment, the processes discussed with reference to FIG. 6 may include fewer or additional blocks and/or the blocks may be performed in order different than is illustrated.

Beginning with block 610, a user requests access to a medical image that was not included in the training data set (discussed above with reference to FIG. 5, for example). For example, a medical professional may request viewing of a medical image of a patient, which may initiate processing of the medical image by the process discussed in FIG. 6. In some implementations, the process of FIG. 6 may be automatically executed, such as in response to acquisition of a new medical image by a medical imaging device, medical record system, and/or other event associated with acquisition, processing, or analysis of the medical image. For example, an x-ray that is acquired in an emergency room setting may automatically be processed by the process outlined in FIG. 6 before the image is viewed by an emergency room doctor.

In block 620, a segmentation algorithm is applied to the medical image to identify segments included in the medical image. At block 630, a segment of the plurality of segments is selected for diagnostic analysis. Depending on the embodiment, the order of selecting segments for diagnostic analysis may vary and/or the diagnostic analysis may be performed partially or fully concurrently for multiple or all segments of a medical image. At block 640, a segment-specific diagnostic model associated with the segment is selected. In some embodiments, other characteristics associated with the medical image (e.g., type of medical image, imaging modality, resolution, size, etc.), patient, etc., may be used in selecting a segment-specific diagnostic model. At block 650, the segment-specific diagnostic model is applied to at least portions of the medical image associated with the segment and the segment-specific diagnostic model provides an indication of whether the segment includes a finding (e.g., an abnormality) or no finding (e.g., no abnormality). For example. The segment-specific diagnostic model may be configured to output a likelihood (e.g., percentage chance) there is an abnormality in the segment or multiple likelihood associated multiple different abnormalities. In some implementations, segment-specific diagnostic models may provide further details regarding a finding. At block 660, the system determines whether additional segments are available for segment-specific diagnostics and, if so, the process returns to block 630 where another segment is selected and then analyzed with a segment-specific diagnostic model in blocks 640 and 650. At block 670 the results of the diagnostic analysis of the image, which may include the results of multiple segment-specific diagnostic models applied to different portions of the image, are stored and/or otherwise provided for user review. For example, the indications of findings (and/or no findings), as well as details regarding any findings, may be included as metadata associated with the medical image, stored in a data structure associated with the medical image, automatically included in a medical report associated with the medical image, and/or stored in any other manner. Thus, a user that subsequently views the medical image (even the first user to ever view the medical image) may already have information regarding findings within segments of the medical image that were determined using segment-specific diagnostic models.

Example Technical Improvements

The systems and methods discussed herein may provide a more effective and efficient means of generating and applying AI algorithms for image analysis, such as without manual image annotation though use of artificial intelligence preprocessing, segmentation, and/or segment analysis. The technical features and advantages main include one or more of:

- Presentation of reports with segmental anatomy listed as finding detected (or "abnormal" or similar) or no finding detected (or "normal" or similar) based on a matching of image segmentation with listed report findings
- Highlighting or outlining of segmented anatomy based on reading physician preferences, so that abnormal (or normal) regions can be reported without diverting attention away from images to the report.
- Automated prompting of the reading physician based on the appropriate listed report finding where an abnormality has been found.
- Classification of imaging findings by preconfigured items for peer reference, public health or other clinical benefits.
- Use by technologists or non-expert physicians to prompt various clinical workflows such as obtaining additional views or determining the need for expert consultation.
- Enable faster and less costly algorithm development as well as a set of RIS/PACS features that differentiate from existing products.

ADDITIONAL IMPLEMENTATION DETAILS AND EMBODIMENTS

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid-state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid-state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

As described above, in various embodiments certain functionality may be accessible by a user through a web-based viewer (such as a web browser), or other suitable software program. In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments may not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A computerized method, performed by a computing system having one or more hardware computer processors and one or more non-transitory computer readable storage device storing software instructions executable by the computing system to perform the computerized method comprising:

for each of a plurality of medical images:

accessing the medical image;

applying a segmentation algorithm to the medical image to determine a plurality of anatomical segments indicated in the medical image, wherein each of the anatomical segments is associated with an anatomical component or an anatomical system;

for each of a plurality of users:

displaying the medical image on a display device of a user;

for each of the plurality of anatomical segments, displaying user interface controls usable to indicate whether a finding is observed by the user;

receiving, via the user interface controls, user input indicating that either:

the anatomical segment shows a finding, or the anatomical segment does not show a finding;

storing, for each anatomical segment, metadata comprising: (i) segment boundaries, (ii) anatomical identifiers, and (iii) user-indicated finding status, in a training data set; and for each of the plurality of anatomical segments:

training a segment-specific diagnostic model to detect findings in the anatomical segment of medical images not included in the plurality of medical images, wherein the segment-specific diagnostic model:

accesses the training data set to identify a first set of medical images with the anatomical segment identified as no finding and a second set of medical images with the anatomical segment identified as finding detected, and trains the segment-specific diagnostic model based on differences between the first and second sets of medical images.

2. The method of claim 1, further comprising:

accessing a medical image not included in the plurality of medical images;

applying the segmentation algorithm to the medical image to determine the plurality of anatomical segments of patient anatomy indicated in the medical image; and for each of the anatomical segments identified in the medical image:

selecting a segment-specific diagnostic model associated with the anatomical segment;

applying the segment-specific diagnostic model to at least portions of the medical image associated with the anatomical segment, wherein the segment-specific diagnostic model provides an indication of whether the anatomical segment is more likely normal or abnormal.

3. The method of claim 2, further comprising:

displaying, in a user interface, an indication of any anatomical segments with findings.

4. The method of claim 2, further comprising:

prepopulating an itemized report with the indications of findings and associated anatomical segments.

5. The method of claim 4, wherein the anatomical segments associated with findings are indicated in the report.

6. The method of claim 4, wherein the anatomical segments associated with findings include a link or reference to a medical image associated with the finding.

7. The method of claim 2, wherein the segment-specific diagnostic model determines indications of finding vs no finding based on one or more of an indication or a clinical question.

8. The method of claim 1, wherein the anatomical components include one or more of: lungs, vasculature, cardiac, mediastinum, pleura, or bone.

9. The method of claim 1, wherein the anatomical systems include one or more of: digestive system, musculoskeletal system, nervous system, endocrine system, reproductive system, urinary system, or immune system.

10. The method of claim 1, wherein the anatomical segments are associated with corresponding sections of a medical report.

11. The method of claim 1, wherein the plurality of anatomical segments are stored in data structure in association with a type of the medical image.

12. The method of claim 1, further comprising:

wherein the segmentation algorithm accesses a medical report associated with the medical image to determine whether there is a finding or no finding for each of the anatomical segments indicating in the medical report.

13. The method of claim 12, wherein said determining whether there is a finding or no finding for each of the anatomical segments indicating in the medical report is based at least partly on natural language processing of textual descriptions associated with respective anatomical segments.

14. The method of claim 1, wherein the segment-specific diagnostic models are trained using itemized reports wherein at least one report item corresponds to an anatomical segment defined in an image.

15. The method of claim 1, wherein the segment-specific diagnostic models are trained using one or more artificial intelligence algorithms to classify items in a medical report as finding or no finding.

16. A computing system comprising:

a hardware computer processor; and a non-transitory computer readable medium having software instructions stored thereon, the software instructions executable by the hardware computer processor to cause the computing system to perform operations comprising:

accessing the medical image;

applying a segmentation algorithm to the medical image to determine a plurality of anatomical segments indicated in the medical image, wherein each of the anatomical segments is associated with an anatomical component or an anatomical system;

for each of a plurality of users:

displaying the medical image on a display device of a user;

for each of the plurality of anatomical segments, displaying user interface controls usable to indicate whether a finding is observed by the user;

receiving, via the user interface controls, user input indicating that either:

the anatomical segment shows a finding, or the anatomical segment does not show a finding;

storing, for each anatomical segment, metadata comprising: (i) segment boundaries, (ii) anatomical identifiers, and (iii) user-indicated finding status, in a training data set; and for each of the plurality of anatomical segments:

training a segment-specific diagnostic model to detect findings in the anatomical segment of medical images not included in the plurality of medical images, wherein the segment-specific diagnostic model:

accesses the training data set to identify a first set of medical images with the anatomical segment identified as no finding and a second set of medical images with the anatomical segment identified as finding detected, and trains the segment-specific diagnostic model based on differences between the first and second sets of medical images.

* * * * *